United States Patent
> Liu et al.

(10) Patent No.: US 11,634,481 B2
(45) Date of Patent: Apr. 25, 2023

(54) **B-CELL EPITOPE OF *TRICHINELLA SPIRALIS* CYSTEINE PROTEASE INHIBITOR, HYBRIDOMA CELL LINE, MONOCLONAL ANTIBODY AND USES THEREOF**

(71) Applicant: JILIN UNIVERSITY, Changchun (CN)

(72) Inventors: Xiaolei Liu, Changchun (CN); Mingyuan Liu, Changchun (CN); Yong Yang, Changchun (CN); Yan Liu, Changchun (CN)

(73) Assignee: JILIN UNIVERSITY, Changchun (CN)

( * ) Notice: Subject to any disclaimer, the term of this patent is extended or adjusted under 35 U.S.C. 154(b) by 208 days.

(21) Appl. No.: 17/128,110

(22) Filed: Dec. 19, 2020

(65) Prior Publication Data

US 2021/0188958 A1 Jun. 24, 2021

(30) Foreign Application Priority Data

Dec. 20, 2019 (CN) .......................... 201911327145.1

(51) Int. Cl.
*C07K 16/20* (2006.01)
*C07K 16/38* (2006.01)
*G01N 33/569* (2006.01)

(52) U.S. Cl.
CPC .............. *C07K 16/20* (2013.01); *C07K 16/38* (2013.01); *G01N 33/56905* (2013.01); *C07K 2317/56* (2013.01); *C07K 2317/565* (2013.01); *G01N 2333/4353* (2013.01); *G01N 2333/8139* (2013.01)

(58) Field of Classification Search
None
See application file for complete search history.

(56) References Cited

FOREIGN PATENT DOCUMENTS

| CN | 102558306 A | 7/2012 |
|----|-------------|--------|
| CN | 105820228 A | 8/2016 |
| CN | 107551265 A | 1/2018 |
| CN | 108088988 A | 5/2018 |
| CN | 110221067 A | 9/2019 |

OTHER PUBLICATIONS

The 1st Office Action dated Mar. 8, 2021 for the Chinese Patent Application No. CN201911327145.1.
X.P. Wu, Identification of antigenic genes in Trichinella spiralis by immunoscreening of cDNA libraries, Veterinary Parasitology vol. 159, Nos. 3-4 (Oct. 22, 2008) 272-275.
Baoquan Fu, Cloning and Sequence Analysis of a cDNA Encoding p46 000 Antigen from Newborn Larvae of Trichinella spiralis, Chin J Vet Sci, Jan. 31, 2005, vol. 25, No. 1, pp. 37-39.
Trichinellosis(infection with *Trichinella* Spp.), OIE Terrestrial Manual 2017, Chapter 2.1.20.
M. Gnjatovic, et al., A competitive enzyme-linked immunosorbent assay for rapid detection of antibodies against Trichinella spiralis and T. britovi—one test for humans and swine, Journal of Helminthology, Oct. 18, 2017.
Bin Tang, et al., Characterisation of a high-frequency gene encoding a strongly antigenic cystatin-like protein from Trichinella spiralis at its early invasion stage, BioMed central, Parasites & Vectors 2015.
Fabrizio Bruschi, et al., International Commission on Trichinellosis: Recommendations on the use of serological tests tor the detection of Trichinella infection in animals and humans, Food and Waterborne Parasitology 12 (2019).
José-Lino Zumaquero-Rios, et al., Trichinella spiralis: Monoclonal antibody against the muscular larvae for the detection of circulating and fecal antigens in experimentally infected rats, Experimental Parasitology 132 (2012) 444-449.
Mingyuan Liu, et al., Trichinellosis in China: epidemiology and control, TRENDS in Parasitology vol. 18 No. 12 Dec. 2002.
Yan Liua, et al., Evaluation of a cystatin-like protein of Trichinella spiralis for serodiagnosis and identification of immunodominant epitopes using monoclonal antibodies, Veterinary Parasitology, Apr. 29, 2020.

*Primary Examiner* — Adam Weidner
(74) *Attorney, Agent, or Firm* — Yue (Robert) Xu; Apex Attorneys at Law, LLP

(57) ABSTRACT

The present disclosure relates to the field of immunology, in particular to a B-cell epitope of *Trichinella spiralis* cysteine protease inhibitor, a hybridoma cell line, a monoclonal antibody and uses thereof. The present disclosure provides a hybridoma cell line that can generate anti-WN10 antibody, and identifies the specific B-cell epitope of WN10 protein recognized by the monoclonal antibody. These are of great significance for the diagnosis of trichinellosis, for the establishment of competitive ELISA for detecting antibodies and sandwich ELSIA for detecting circulating antigens, for the detection of *Trichinella spiralis* in different hosts and for the development of subunit vaccines.

6 Claims, 4 Drawing Sheets

Specification includes a Sequence Listing.

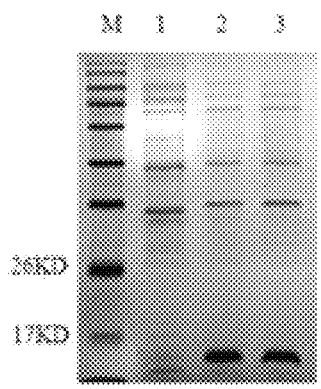
FIG. 7
FIG. 8
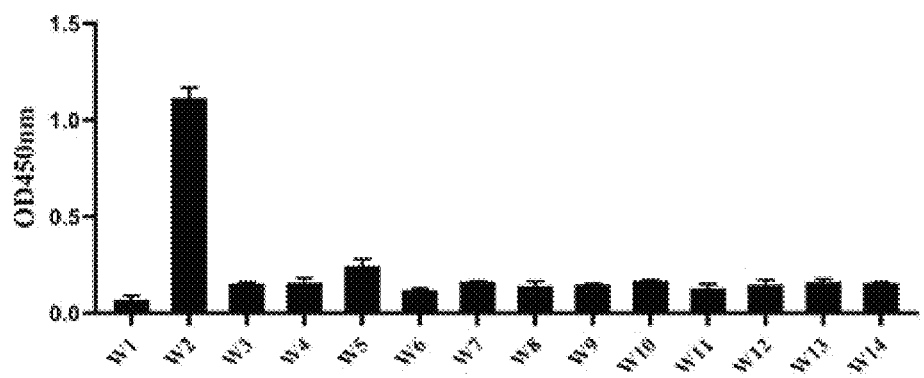
FIG. 9

SEQUENCE LISTING

<160> NUMBER OF SEQ ID NOS: 36

<210> SEQ ID NO 1
<211> LENGTH: 15
<212> TYPE: PRT
<213> ORGANISM: Trichinella spiralis

<400> SEQUENCE: 1

Val Asn Cys Gln Gly Glu Gly Arg Arg Lys His Cys Thr Met Glu
1               5                   10                  15

<210> SEQ ID NO 2
<211> LENGTH: 45
<212> TYPE: DNA
<213> ORGANISM: Trichinella spiralis

```
<400> SEQUENCE: 2
gttaattgtc aaggagaagg ccgacgaaag cattgtacaa tggaa            45

<210> SEQ ID NO 3
<211> LENGTH: 27
<212> TYPE: DNA
<213> ORGANISM: Artificial
<220> FEATURE:
<223> OTHER INFORMATION: TsWN10-EcoRI-atg primer

<400> SEQUENCE: 3
taacgaattc atgcagatac ttggtga                                27

<210> SEQ ID NO 4
<211> LENGTH: 23
<212> TYPE: DNA
<213> ORGANISM: Artificial
<220> FEATURE:
<223> OTHER INFORMATION: TsWN10-XhoI-tta primer

<400> SEQUENCE: 4
gacgctcgag ttaacattca aca                                    23

<210> SEQ ID NO 5
<211> LENGTH: 27
<212> TYPE: DNA
<213> ORGANISM: Artificial
<220> FEATURE:
<223> OTHER INFORMATION: TsWN10-A-EcoRI-atg primer

<400> SEQUENCE: 5
taacgaattc atgcagatac ttggtga                                27

<210> SEQ ID NO 6
<211> LENGTH: 23
<212> TYPE: DNA
<213> ORGANISM: Artificial
<220> FEATURE:
<223> OTHER INFORMATION: TsWN10-A-XhoI-tta primer

<400> SEQUENCE: 6
gacgctcgag ttaattcacc ctt                                    23

<210> SEQ ID NO 7
<211> LENGTH: 25
<212> TYPE: DNA
<213> ORGANISM: Artificial
<220> FEATURE:
<223> OTHER INFORMATION: TsWN10-B-EcoRI-atg primer

<400> SEQUENCE: 7
taacgaattc atgcgtgtcc aaagg                                  25

<210> SEQ ID NO 8
<211> LENGTH: 23
<212> TYPE: DNA
<213> ORGANISM: Artificial
<220> FEATURE:
<223> OTHER INFORMATION: TsWN10-B-XhoI-tta primer

<400> SEQUENCE: 8
gacgctcgag ttaacattca aca                                    23

<210> SEQ ID NO 9
```

```
<211> LENGTH: 23
<212> TYPE: DNA
<213> ORGANISM: Artificial
<220> FEATURE:
<223> OTHER INFORMATION: TsWN10-A01-EcoRI-atg primer

<400> SEQUENCE: 9
taacgaattc atgcagatac ttg                                              23

<210> SEQ ID NO 10
<211> LENGTH: 23
<212> TYPE: DNA
<213> ORGANISM: Artificial
<220> FEATURE:
<223> OTHER INFORMATION: TsWN10-A01-XhoI-tta primer

<400> SEQUENCE: 10
gacgctcgag ttaagcattt gaa                                              23

<210> SEQ ID NO 11
<211> LENGTH: 27
<212> TYPE: DNA
<213> ORGANISM: Artificial
<220> FEATURE:
<223> OTHER INFORMATION: TsWN10-A02-EcoRI-atg primer

<400> SEQUENCE: 11
taacgaattc atgattgatt caaatgc                                          27

<210> SEQ ID NO 12
<211> LENGTH: 23
<212> TYPE: DNA
<213> ORGANISM: Artificial
<220> FEATURE:
<223> OTHER INFORMATION: TsWN10-A02-XhoI-tta primer

<400> SEQUENCE: 12
gacgctcgag ttaattcacc ctt                                              23

<210> SEQ ID NO 13
<211> LENGTH: 388
<212> TYPE: PRT
<213> ORGANISM: Trichinella spiralis

<400> SEQUENCE: 13

Gln Ile Leu Gly Glu Thr Thr His Tyr Gly Arg Asn Asp Pro Val Met
1               5                   10                  15

Leu Arg Asn Ala His Glu Ala Leu Phe Ser Ser Asp Leu Lys Gln Glu
            20                  25                  30

Ser Gly Val Phe His Lys Leu Leu Glu Leu Glu Glu Ser Ser Thr Met
        35                  40                  45

Gly Ile Leu Thr Thr Met Lys Val Val Met Gln Asp Thr Asp Cys Pro
    50                  55                  60

Val Ser Phe Ala Leu Leu Ser Tyr Tyr Asp Val Leu Val Asn Cys Gln
65                  70                  75                  80

Gly Glu Gly Arg Arg Lys His Cys Thr Met Glu Tyr Thr His Arg Asn
                85                  90                  95

Pro Ser Lys Ala Thr Val Ser Lys Cys Phe Glu Val Glu Glu Pro
            100                 105                 110

Leu Ile Ile Pro Gln Arg Val Lys Met Ile Gly Gly Arg Ala Val Tyr
        115                 120                 125

Ile Asp Ser Asn Ala Asp Val Glu Glu Gln Met Gln Met Leu Gly Glu
```

|       |       | 130   |       |       | 135   |       |       | 140   |       |       |       |
|-------|-------|-------|-------|-------|-------|-------|-------|-------|-------|-------|-------|

Thr Thr His Tyr Gly Arg Asn Asp Pro Val Met Leu Pro Lys Ala Arg
145                 150                 155                 160

Glu Ala Leu Phe Ser Ser Asp Ser Lys Glu Gln Ser Gly Val Leu His
            165                 170                 175

Lys Leu Val Glu Leu Glu Glu Ser Ser Thr Met Gly Ile Leu Thr Thr
            180                 185                 190

Met Lys Val Val Ile Gln Asp Thr Glu Cys Arg Val Ser Ser Ala Tyr
            195                 200                 205

Ser Ser Tyr Tyr Asp Val Leu His Tyr Cys His Gly Lys Gly Pro Arg
    210                 215                 220

Lys His Cys Thr Leu Glu Tyr Arg His Arg Thr Pro Ser Thr Ala Thr
225                 230                 235                 240

Val Ser Glu Cys Phe Glu Glu Val Glu Glu Pro Leu Ile Val Pro Gln
            245                 250                 255

Arg Val Gln Arg Val Asn Gly Arg Thr Ile Tyr Leu Asp Ser Ser Asp
            260                 265                 270

Asp Val Glu Glu Gln Val Val Ser Gln Arg Ser Gln Met Leu Gly Gly
            275                 280                 285

Thr Thr Lys Tyr Thr Asp Ser Asn Val His Ile Lys Glu Glu Val Lys
290                 295                 300

Gln Ala Ile Phe Glu Ser Asp Lys Lys Ser Ser Gly Thr Tyr Leu
305                 310                 315                 320

Leu Leu Asp Lys Ile Val Glu Gly Phe Asn Met Gly Ile Ser Ser Arg
            325                 330                 335

Phe Gln Val Leu Val Lys Glu Thr Glu Cys Gly Ile Lys Glu Lys Ala
            340                 345                 350

Phe Asn Ser Tyr Glu Asp Val Tyr Lys Asn Cys Ser Gly Ser Gly Asp
            355                 360                 365

Ser Lys Val Cys Ser Val Glu Tyr Lys Tyr Phe Asp Pro Thr Lys Ser
            370                 375                 380

Thr Val Glu Cys
385

<210> SEQ ID NO 14
<211> LENGTH: 1167
<212> TYPE: DNA
<213> ORGANISM: Trichinella spiralis

<400> SEQUENCE: 14
cagatacttg gtgaaacaac tcactatggt agaaatgatc ctgtcatgtt gcgaaatgcg      60
catgaggcat tattttcatc ggacttgaaa caagaatcag gtgtatttca caaactctta     120
gaacttgaag aaagttcaac catgggaatc cttactacca tgaaagtcgt tatgcaagat     180
actgattgcc cagtttcatt cgcactttta tcatattacg atgtactagt taattgtcaa     240
ggagaaggcc gacgaaagca ttgtacaatg aatataccc atcgcaatcc ttcaaaagca     300
actgtcagca atgtttcga gaagtagaa gagccattaa ttataccgca acgtgtcaaa     360
atgataggtg aagggcagt atatattgat tcaaatgctg atgtagaaga acagatgcag     420
atgcttggtg aaacaactca ctatggtaga atgatcctg tcatgttgcc aaaagcgcgg     480
gaagcattat tctcatcaga ctcgaaagaa caatcaggtg tattgcacaa gctcgtagaa     540
cttgaagaaa gttcaaccat gggaatcctt actaccatga agtcgttat acaagatact     600 gaatgccgag tttcatccgc atattcttca tattacgatg tactacatta ctgtcacggt     660

```
aaaggcccac ggaagcactg tacattggaa tatagacatc gcactccttc aacagcaact    720
gtcagcgaat gttttgaaga agtagaagaa ccattaattg taccgcaacg tgtccaaagg    780
gtgaatggaa gaacgatata tcttgattca agtgatgatg tagaagaaca ggttgtatca    840
caacgtagcc aaatgttggg tggaacaaca aaatacactg attcaaatgt tcatataaaa    900
gaagaagtaa agcaagctat attcgaatca gataagaaga aatcaagcgg aacatatctt    960
ctgttggata aaattgtaga gggttttaat atgggaatat cttcccgttt tcaagtttta   1020
gtgaaagaaa cagaatgcgg tattaaagag aaagcattca attcttatga ggatgtttat   1080
aaaaactgtt ctggttctgg agattcgaaa gtgtgctccg ttgaatacaa atatttcgat   1140
ccaaccaagt caactgttga atgttaa                                       1167
```

<210> SEQ ID NO 15
<211> LENGTH: 111
<212> TYPE: PRT
<213> ORGANISM: Artificial
<220> FEATURE:
<223> OTHER INFORMATION: Light chain variable region

<400> SEQUENCE: 15

```
Asp Val Val Val Thr Gln Ser Pro Ala Ser Leu Ala Val Ser Leu Gly
1               5                   10                  15

Gln Arg Ala Thr Ile Ser Cys Arg Ala Ser Lys Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ile Lys
                85                  90                  95

Glu Val Pro Tyr Thr Phe Gly Gly Gly Thr Lys Leu Glu Ile Lys
            100                 105                 110
```

<210> SEQ ID NO 16
<211> LENGTH: 115
<212> TYPE: PRT
<213> ORGANISM: Artificial
<220> FEATURE:
<223> OTHER INFORMATION: Heavy chain variable region

<400> SEQUENCE: 16

```
Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Ser Pro Gly Ser Gly Asn Thr Asn Tyr Asp Glu Lys Phe
    50                  55                  60

Lys Thr Lys Ala Thr Leu Thr Val Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg His Gly Thr Val Asp Tyr Trp Gly Gln Gly Thr Thr Val Thr
```

Val Ser Ser
    115

<210> SEQ ID NO 17
<211> LENGTH: 10
<212> TYPE: PRT
<213> ORGANISM: Artificial
<220> FEATURE:
<223> OTHER INFORMATION: CDR-L1

<400> SEQUENCE: 17

Lys Ser Val Asp Asn Tyr Gly Ile Ser Phe
1               5                   10

<210> SEQ ID NO 18
<211> LENGTH: 3
<212> TYPE: PRT
<213> ORGANISM: Artificial
<220> FEATURE:
<223> OTHER INFORMATION: CDR-L2

<400> SEQUENCE: 18

Ala Ala Ser
1

<210> SEQ ID NO 19
<211> LENGTH: 9
<212> TYPE: PRT
<213> ORGANISM: Artificial
<220> FEATURE:
<223> OTHER INFORMATION: CDR-L3

<400> SEQUENCE: 19

Gln Gln Ile Lys Glu Val Pro Tyr Thr
1               5

<210> SEQ ID NO 20
<211> LENGTH: 8
<212> TYPE: PRT
<213> ORGANISM: Artificial
<220> FEATURE:
<223> OTHER INFORMATION: CDR-H1

<400> SEQUENCE: 20

Gly Tyr Thr Phe Thr Ser Tyr Trp
1               5

<210> SEQ ID NO 21
<211> LENGTH: 8
<212> TYPE: PRT
<213> ORGANISM: Artificial
<220> FEATURE:
<223> OTHER INFORMATION: CDR-H2

<400> SEQUENCE: 21

Ile Ser Pro Gly Ser Gly Asn Thr
1               5

<210> SEQ ID NO 22
<211> LENGTH: 8
<212> TYPE: PRT
<213> ORGANISM: Artificial
<220> FEATURE:
<223> OTHER INFORMATION: CDR-H3

<400> SEQUENCE: 22

Thr Arg His Gly Thr Val Asp Tyr
1               5

<210> SEQ ID NO 23
<211> LENGTH: 15
<212> TYPE: PRT
<213> ORGANISM: Artificial
<220> FEATURE:
<223> OTHER INFORMATION: Peptide W1

<400> SEQUENCE: 23

Ala Leu Phe Ser Ser Asp Leu Lys Gln Glu Ser Gly Val Phe His
1               5                   10                  15

<210> SEQ ID NO 24
<211> LENGTH: 15
<212> TYPE: PRT
<213> ORGANISM: Artificial
<220> FEATURE:
<223> OTHER INFORMATION: Peptide W2

<400> SEQUENCE: 24

Val Asn Cys Gln Gly Glu Gly Arg Arg Lys His Cys Thr Met Glu
1               5                   10                  15

<210> SEQ ID NO 25
<211> LENGTH: 15
<212> TYPE: PRT
<213> ORGANISM: Artificial
<220> FEATURE:
<223> OTHER INFORMATION: Peptide W3

<400> SEQUENCE: 25

Thr Met Glu Tyr Thr His Arg Asn Pro Ser Lys Ala Thr Val Ser
1               5                   10                  15

<210> SEQ ID NO 26
<211> LENGTH: 15
<212> TYPE: PRT
<213> ORGANISM: Artificial
<220> FEATURE:
<223> OTHER INFORMATION: Peptide W4

<400> SEQUENCE: 26

Thr Val Ser Lys Cys Phe Glu Glu Val Glu Glu Pro Leu Ile Ile
1               5                   10                  15

<210> SEQ ID NO 27
<211> LENGTH: 14
<212> TYPE: PRT
<213> ORGANISM: Artificial
<220> FEATURE:
<223> OTHER INFORMATION: Peptide W5

<400> SEQUENCE: 27

Gln Ile Leu Gly Glu Thr Thr His Tyr Gly Arg Asn Asp Pro
1               5                   10

<210> SEQ ID NO 28
<211> LENGTH: 15
<212> TYPE: PRT
<213> ORGANISM: Artificial
<220> FEATURE:
<223> OTHER INFORMATION: Peptide W6

<400> SEQUENCE: 28

```
Ala Leu Phe Ser Ser Asp Ser Lys Glu Gln Ser Gly Val Leu His
1               5                   10                  15

<210> SEQ ID NO 29
<211> LENGTH: 15
<212> TYPE: PRT
<213> ORGANISM: Artificial
<220> FEATURE:
<223> OTHER INFORMATION: Peptide W7

<400> SEQUENCE: 29

His Lys Leu Val Glu Leu Glu Glu Ser Ser Thr Met Gly Ile Leu
1               5                   10                  15

<210> SEQ ID NO 30
<211> LENGTH: 15
<212> TYPE: PRT
<213> ORGANISM: Artificial
<220> FEATURE:
<223> OTHER INFORMATION: Peptide W8

<400> SEQUENCE: 30

Cys Thr Leu Glu Tyr Arg His Arg Thr Pro Ser Thr Ala Thr Val
1               5                   10                  15

<210> SEQ ID NO 31
<211> LENGTH: 15
<212> TYPE: PRT
<213> ORGANISM: Artificial
<220> FEATURE:
<223> OTHER INFORMATION: Peptide W9

<400> SEQUENCE: 31

Glu Glu Gln Val Val Ser Gln Arg Ser Gln Met Leu Gly Gly Thr
1               5                   10                  15

<210> SEQ ID NO 32
<211> LENGTH: 15
<212> TYPE: PRT
<213> ORGANISM: Artificial
<220> FEATURE:
<223> OTHER INFORMATION: Peptide W10

<400> SEQUENCE: 32

Ile Phe Glu Ser Asp Lys Lys Lys Ser Ser Gly Thr Tyr Leu Leu
1               5                   10                  15

<210> SEQ ID NO 33
<211> LENGTH: 15
<212> TYPE: PRT
<213> ORGANISM: Artificial
<220> FEATURE:
<223> OTHER INFORMATION: Peptide W11

<400> SEQUENCE: 33

Lys Glu Thr Glu Cys Gly Ile Lys Glu Lys Ala Phe Asn Ser Tyr
1               5                   10                  15

<210> SEQ ID NO 34
<211> LENGTH: 15
<212> TYPE: PRT
<213> ORGANISM: Artificial
<220> FEATURE:
<223> OTHER INFORMATION: Peptide W12

<400> SEQUENCE: 34

Glu Lys Ala Phe Asn Ser Tyr Glu Asp Val Tyr Lys Asn Cys Ser
```

-continued

```
<210> SEQ ID NO 35
<211> LENGTH: 15
<212> TYPE: PRT
<213> ORGANISM: Artificial
<220> FEATURE:
<223> OTHER INFORMATION: Peptide W13

<400> SEQUENCE: 35

Asp Val Tyr Lys Asn Cys Ser Gly Ser Gly Asp Ser Lys Val Cys
1               5                   10                  15

<210> SEQ ID NO 36
<211> LENGTH: 15
<212> TYPE: PRT
<213> ORGANISM: Artificial
<220> FEATURE:
<223> OTHER INFORMATION: Peptide W14

<400> SEQUENCE: 36

Val Glu Tyr Lys Tyr Phe Asp Pro Thr Lys Ser Thr Val Glu Cys
1               5                   10                  15
```

B-CELL EPITOPE OF *TRICHINELLA SPIRALIS* CYSTEINE PROTEASE INHIBITOR, HYBRIDOMA CELL LINE, MONOCLONAL ANTIBODY AND USES THEREOF

CROSS REFERENCE TO RELATED APPLICATIONS

This application claims the priority of Chinese Patent Application No. 201911327145.1, filed on Dec. 20, 2019, and the disclosures of which are hereby incorporated by reference.

FIELD

The present disclosure relates to the field of immunology, in particular to a B-cell epitope of *Trichinella spiralis* cysteine protease inhibitor, a hybridoma cell line, a monoclonal antibody and uses thereof.

BACKGROUND

Trichinellosis is mainly caused by eating raw or undercooked meat containing *Trichinella spiralis*, and infected pork is the main source for human infection. The average incubation period of human trichinellosis is two weeks. The main symptoms of patients in the acute phase are fever, severe muscle pain, severe diarrhea, facial edema, and eosinophilia. Symptoms may last for several weeks and lead to body failure. In particular, severely infected people may experience severe damage to the myocardium and brain, and even death.

In view of the great threat and harm that *Trichinella spiralis* poses to public health safety, the World Organization for Animal Health, formerly the Office International des Epizooties (OLE), has listed trichinellosis as a compulsory inspection of slaughtered animals and a mandatory inspection for the primary inspection. For the inspection of trichinellosis in slaughtered animals, the standard inspection methods required by the International Organization for Animal Health are microscopic inspection and sample digestion assay. At present, these two methods are also used in China. However, the above two methods have certain drawbacks. The microscopy inspection is time-consuming and labor-intensive and has poor sensitivity, of which the sensitivity is only when the density of larvae in the meat reaches 3 larvae per gram. Although the digestion assay can greatly increase the detection rate, the detection rate can be increased to 1 worm per gram of meat, the method is still very cumbersome, and the positive group still needs to be tested one by one when a positive sample is found. From a sensitivity point of view, the missing positive samples from microscopy inspection and digestion assay have safety hazards and may cause human infections (ingestion of 75 larvae will cause human infection).

Researchers at home and abroad have conducted a lot of research on the immunological detection of *Trichinella spiralis*, such as indirect fluorescent immunoassay, immunoenzyme staining test, western blotting test, enzyme-linked immunosorbent assay (ELISA), etc. Among them, the enzyme-linked immunosorbent assay (ELISA) is the most commonly used immunological method for the detection of *Trichinella spiralis* infection. It has high sensitivity and the detection limit can be as low as one larva per 100 g of muscle tissue. At present, excretion/secretion (ES) antigens of *Trichinella spiralis* muscle larvae are the only standard antigen for serological antibody detection prescribed by OIE and the International Commission on Trichinellosis. However, the components of ES antigens are complex, the preparation is complicated, the production cycle is long, batch quality is inconsistent, and there is cross-reaction. In addition, there is serious diagnostic blind spot, because this method cannot detect out trichinellosis until 19 days after the infection. All these hinder its practical application. Therefore, screening specific and sensitive *Trichinella spiralis* antigens, using genetic engineering technology to prepare recombinant antigens to reduce the difficulty of antigen preparation, and establishing a specific pig trichinellosis serological detection method without blind spots has become the research focus of many researchers at home and abroad.

There is an urgent need to develop new reagents for the detection of *Trichinella spiralis*.

SUMMARY

The inventors carried out immunological screening on the cDNA expression library after 6 hours of *Trichinella spiralis* infection, and successfully obtained an antigen protein gene with highly abundance and highly reactivity, named *Trichinella spiralis* WN10 (Ts-WN10 or WN10), which encodes a cysteine protease inhibitor. WN10 gene accession number (Genbank) is EU263325, protein accession number (Genbank) is ABY60755. Further immunoblotting and indirect ELSIA showed that the recombinant WN10 antigen expressed in prokaryotic cells can be recognized by the sera of pigs infected with *Trichinella spiralis* for 17, 25 and 60 days, indicating that WN10 is an ideal candidate antigen for the serological detection of *Trichinella spiralis* and can be used for improving serological testing methods.

Furthermore, the hybridoma cell lines secreting specific antibody against Ts-WN10 protein was screened out, and the specific B-cell epitope recognized by the obtained monoclonal antibody was identified, which has positive influence on the diagnosis and prevention of trichinellosis, and laid the foundation for the development of *Trichinella spiralis* subunit vaccine.

Based on the above, the present disclosure provides a B-cell epitope of Ts-WN10 protein, a hybridoma cell line, a monoclonal antibody and uses thereof. The present disclosure provides a hybridoma cell line that can secrete anti-WN10 specific antibody, and identifies the specific B-cell epitope of WN10 protein, which is recognized by the secreted monoclonal antibodies. These are of great significance for the diagnosis of trichinellosis, for the establishment of competitive ELISA and sandwich ELSIA for detecting circulating antigens, for the detection of *Trichinella spiralis* in different hosts and for the development of subunit vaccines.

In order to achieve the above-mentioned purpose, the present disclosure provides the following technical solutions The present disclosure provides a B-cell epitope of Ts-WN10 protein, comprising (I) an amino acid sequence set forth in SEQ ID No: 1;

(II) an amino acid sequence obtained by adding, deleting, or replacing one or two amino acids in the amino acid sequence of (I), which has the same or similar functions as the amino acid sequence of (I); or (III) an amino acid sequence having at least 90% identity to the amino acid sequence of (I) or (II), which has the same or similar functions as the amino acid sequence of (I).

The present disclosure also provides a nucleic acid encoding the B-cell epitope of WN10, comprising (I) a nucleotide sequence set forth in SEQ ID No: 2;

(II) a complementary nucleotide sequence of the nucleotide sequence set forth in SEQ ID No: 2;

(III) a nucleotide sequence encoding the same protein as the nucleotide sequence of (I) or (II), which has different nucleotide sequence from (I) or (II) due to degeneracy of genetic code;

(IV) a nucleotide sequence obtained by adding, deleting, or replacing one or two nucleotides in the nucleotide sequence of (I), (II) or (III), which has the same or similar functions as the nucleotide sequence of (I), (II) or (III); or (V) a nucleotide sequence having at least 90% identity to the nucleotide sequence of (I), (II), (III) or (IV).

Further, the present disclosure provides a recombinant expression vector comprising the above-mentioned nucleic acids.

Further, the present disclosure provides a recombinant bacterium or cell comprising the above-mentioned nucleic acids.

On the basis of the above research, the present disclosure also provides uses of the B-cell epitope of Ts-WN10 in the preparation of a detection reagent for *Trichinella spiralis* infection, a detection kit for *Trichinella spiralis* infection, or a vaccine for the prevention of *Trichinella spiralis* infection.

Further, the present disclosure provides a hybridoma cell line with a deposition number of CGMCC No. 18316.

The present disclosure also provides a monoclonal antibody, wherein (I) the monoclonal antibody is generated by the hybridoma cell line with deposition number of CGMCC No. 18316;

(II) the monoclonal antibody is capable of binding to the same epitope to which the monoclonal antibody generated by the hybridoma cell line with deposition number of CGMCC No. 18316 binds;

(III) the monoclonal antibody generated by the hybridoma cell line with deposition number of CGMCC No. 18316 is capable of competing with the *Trichinella spiralis* positive sera of pig in competition binding assay; or (IV) the monoclonal antibody comprises an antigen-binding fragment of any one of the monoclonal antibodies of (I) to (III), and wherein the antigen-binding fragment is capable of specifically binding to the WN10 protein or a variant thereof.

The present disclosure also provides uses of the hybridoma cell line or the monoclonal antibody in the preparation of a detection reagent for *Trichinella spiralis* infection and a detection kit for *Trichinella spiralis* infection.

The antibody or antigen-binding fragment thereof provided by the present disclosure comprises a CDR-L1, a CDR-L2, and a CDR-L3 in a light chain variable region, and a CHR-H1, a CDR-H2, and a CDR-H3 in a heavy chain variable region, wherein the CDR-L1, CDR-L2 and CDR-L3 have an amino acid sequence set forth in SEQ ID NOs: 17, 18 and 19, respectively, and wherein the CDR-H1, CDR-H2 and CDR-H3 have an amino acid sequence set forth in SEQ ID NOs: 20, 21 and 22, respectively.

Specifically, the antibody or antigen-binding fragment comprises a light chain variable region with a sequence set forth in SEQ ID NO: 15 and a heavy chain variable region with a sequence set forth in SEQ ID NO: 16.

In an embodiment of the present disclosure, the antibody comprises a constant region sequence of mouse IgG1.

In another embodiment of the present disclosure, the antigen-binding fragment comprises one or more selected from the group consisting of F(ab')$_2$, Fab', Fab, Fv and scFv.

The present disclosure also provides a detection reagent for *Trichinella spiralis* infection and a detection kit for *Trichinella spiralis* infection, which comprises the hybridoma cell line or the monoclonal antibody, and an acceptable excipient in testing.

The excretion/secretion (ES) antigens of *Trichinella spiralis* muscle larvae are the only standard antigen for serological antibody detection prescribed by OIE and the International Commission on Trichinellosis. However, the components of ES antigens are complex, the preparation is complicated, the production cycle is long, batch quality is inconsistent, and there is cross-reaction. In addition, there is serious diagnostic blind spot, because this method cannot detect out trichinellosis until 19 days after the infection. All these hinder its practical application. Monoclonal antibodies have the advantages of strong binding specificity to antigen, good purity, strong reproducibility, easy quality control, good affinity and being suitable for large-scale production, so they are widely used in immunological detection methods.

The present disclosure obtains a hybridoma cell line that can secrete specific antibodies against Ts-WN10 protein, and identifies the specific B-cell epitope of Ts-WN10 recognized by the monoclonal antibody. These results are of great significance for the diagnosis of trichinellosis, for the establishment of competitive ELISA and sandwich ELSIA for detecting circulating antigens, for the detection of *Trichinella spiralis* in different hosts and for the development of subunit vaccines.

Materials Deposition

Material: WN10-1H9, taxonomic name: hybridoma cell line, which was deposited at China General Microbiological Culture Collection Center (CGMCC) with an accession number 18316 on Aug. 15, 2019, wherein the address of China General Microbiological Culture Collection Center (CGMCC) is No. 1 Beichen West Road, Chaoyang District, Beijing, China.

BRIEF DESCRIPTION OF DRAWINGS

In order to explain the embodiments of the present disclosure or the technical solutions in the prior art more clearly, the followings are briefly introduction of the drawings used in the description of the embodiments or the prior art.

Figure 1:
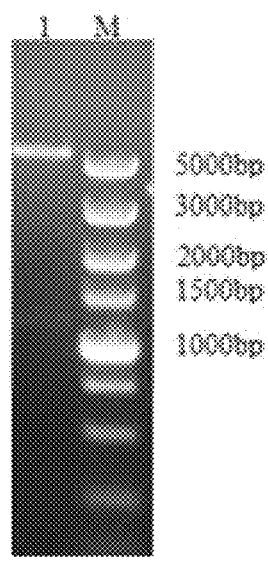
FIG. 1 shows the results of PCR amplification; M, DNA molecular marker; 1, Ts-WN10 amplification product.

4, Western blot result of 1H9 and total protein of BL21-pET28a after IPTG induction.

FIG. 7 shows the SDS-PAGE analysis of Ts-WN10-A01 and Ts-WN10-A02 proteins. M, protein molecular marker; 1, BL21-pET28a (after IPTG induction); 2, BL21-pET28a-WN10-A01 (after IPTG induction); 3, BL21-pET28a-WN10-A02 (after IPTG induction).

FIG. 8 shows the Western blot analysis of WN10-A01 and WN10-A02. M, protein molecular marker; 1, Western blot result of BL21-pET28a (after induction) and 1H9; 2, Western blot result of WN10-A01 and 1H9; 3, Western blot result of WN10-A02 and 1H9.

FIG. 9 shows the ELISA results of synthetic small peptides W1-W14 recognized by 1H9.

DETAILED DESCRIPTION

The present disclosure provides a B-cell epitope of *Trichinella spiralis* cysteine protease inhibitor, a hybridoma cell line, a monoclonal antibody and uses thereof. Those skilled in the art can learn from the content of this article and appropriately improve the process parameters to realize the present invention. In particular, it should be pointed out that all similar substitutions and modifications are obvious to those skilled in the art, and they are all deemed to be included in the present invention. The method and application of the present invention have been described through the preferred embodiments. It is obvious that relevant persons can modify or appropriately change and combine the methods and applications described herein without departing from the content, spirit and scope of the present invention to achieve the present invention.

One object of the present disclosure is to provide a hybridoma cell line that secretes monoclonal antibody against Ts-WN10 protein.

Another object of the present disclosure is to provide a monoclonal antibody secreted by the aforementioned hybridoma cell line. The monoclonal antibody can specifically react with the Ts-WN10 protein, and can compete with the positive sera of pig infected with *Trichinella spiralis* to recognize the recombinant Ts-WN10 antigen.

Another object of the present disclosure is to identify a specific B-cell epitope of Ts-WN10 protein. The Ts-WN10 amino acid sequence (without signal peptide) used in the present disclosure is set forth in SEQ IN NO: 13 as

```
QILGETTHYGRNDPVMLRNAHEALFSSDLKQESGVFHKLLELEESSTMGI
LTTMKVVMQDTDCPVSFALLSYYDVLVNCQGEGRRKHCTMEYTHRNPSKA
TVSKCFEEVEEPLIIPQRVKMIGGRAVYIDSNADVEEQMQMLGETTHYGR
NDPVMLPKAREALFSSDSKEQSGVLHKLVELEESSTMGILTTMKVVIQDT
ECRVSSAYSSYYDVLHYCHGKGPRKHCTLEYRHRTPSTATVSECFEEVEE
PLIVPQRVQRVNGRTIYLDSSDDVEEQVVSQRSQMLGGTTKYTDSNVHIK
EEVKQAIFESDKKKSSGTYLLLDKIVEGFNMGISSRFQVLVKETECGIKE
KAFNSYEDVYKNCSGSGDSK VCSVEYKYFDPTKSTVEC.
```

In the present disclosure, the total RNA of *Trichinella spiralis* was extracted using TRIZOL, and then the WN10 cDNA fragment (SEQ IN NO: 14) was cloned by reverse transcription. The cDNA was inserted into the prokaryotic expression vector pET28a, and Ts-WN10 was expressed using the pET28a prokaryotic expression vector. The expressed Ts-WN10 protein in the form of inclusion bodies was isolated and purified, and used as an immunogen to immunize BALB/c mice, and then spleen cells were fused with SP2/0 myeloma cells. In addition, the Ts-WN10 protein was purified by one-step on-column purification using Ni column and AKTA protein purification system. The purified Ts-WN10 was used as the antigen for detection, and also in the indirect ELISA detection to screen positive hybridoma cells. In addition, the positive hybridoma cells were screened again according to the indirect ELISA method recommended in the standard OIE Terrestrial Manual 2017, Chapter 2.1.20-Trichinellosis. Finally, a hybridoma cell line that stably generates monoclonal antibody against Ts-WN10 was obtained.

The present disclosure also provides a monoclonal antibody generated by the aforementioned hybridoma cell line WN10-1H9, which was named WN10-1H9-Ab (1H9 for short). Competitive ELISA test results showed that the monoclonal antibody WN10-1H9-Ab can compete with *Trichinella spiralis*-infected pig serum to bind Ts-WN10. Western blot results showed that the monoclonal antibody prepared by the present disclosure can specifically bind to the soluble antigen of *Trichinella spiralis* (*T. spiralis*) muscle larvae.

The present disclosure uses peptide scanning assay to identify the B-cell epitope recognized by WN10-1H9, and determines that the epitope recognized by WN10-1H9-Ab is VNCQGEGRRKHCTME (as shown in SEQ ID No: 1).

The corresponding nucleotide sequence is

```
                                          (SEQ ID No: 2)
GTTAATTGTCAAGGAGAAGGCCGACGAAAGCATTGTACAATGGAA.
```

The present disclosure provides uses of the hybridoma cell line in the detection of *Trichinella spiralis* infection, and the uses of B-cell epitope of Ts-WN10 in the detection of *Trichinella spiralis* infection.

In summary, the present disclosure has prepared and identified a monoclonal antibody against Ts-WN10 protein. The monoclonal antibody and the B-cell epitope of Ts-WN10 recognized by the monoclonal antibody can be used to prepare diagnostic reagent for *Trichinella spiralis* infection, which has laid the foundation for the establishment of a serological diagnosis method for *Trichinella spiralis*.

Materials

1. Proteins, Cells, Worms

The Ts-WN10 protein was expressed in prokaryotic cells and purified by gel separation. The Ts-WN10 protein expressed in prokaryotic cells was further purified by one-step on-column purification and refolding. SP2/0 cells was obtained from National Collection of Authenticated Cell Cultures (Cat. TCM18) and *Trichinella spiralis* (strain ISS534) species is preserved in the lab oratory.

2. Reagents

Purification column HisTrap™ HP (packed with Ni Sepharose High Performance (HP) affinity resin) was purchased from GE, USA; fetal bovine serum and 1640 medium were purchased from Biological Industries; HAT medium (50×), HT medium (50×) and antibody subclass identification kit were purchased from sigma; soluble TMB substrate solution was purchased from TIANGEN; horseradish peroxidase (HRP)-labeled goat anti-mouse IgG antibody was purchased from Beijing Bioss; pre-stained protein marker was purchased from Fermentas; restriction endonucleases EcoRI and XhoI, reverse transcriptase, Ex Taq DNA polymerase, and T4 DNA ligase were purchased from TaKaRa (Dalian)

Co., Ltd; ECL luminescent substrate was purchased from Solarbio Life Sciences (Beijing).

3. Experimental Animals

BALB/c mice aged 6 weeks were provided by Changchun Yisi Experimental Animal Technology Co., Ltd.

In the following, the present disclosure will be further explained in conjunction with the examples.

EXAMPLES

Example 1 Prokaryotic Expression and Purification of Ts-WN10 Protein

1. Primer Design

According to the Ts-WN10 gene sequence registered in Genbank (accession number: EU263325), PCR amplification primers were designed. The sequences are as follows:

```
TsWN10-EcoRI-atg:
5'-TAACGAATTCATGCAGATACTTGGTGA-3'
(as shown in SEQ ID No: 3);

TsWN10-XhoI-tta:
5'-GACGCTCGAGTTAACATTCAACA-3'
(as shown in SEQ ID No: 4).
```

The underlined parts are the introduced EcoRI and XhoI restriction sites, and the length of the amplified product is expected to be 1187 bp.

2. RNA Extraction from *Trichinella spiralis* T1 and Reverse Transcription

The mouse carrying *Trichinella spiralis* (strain ISS534) was killed by cervical dislocation, and the skin, tail, internal organs and claws were removed. The body was washed and minced, placed in 300 ml of digestion solution containing 1% HCl and 1% pepsin, and stirred and digested in a 37° C. incubator for 2 hours. The digestion solution was filtered with 80-mesh filter to remove the residues, and the filtrate was collected after 2 hours of precipitation in a separatory funnel, about 500 ml. After the filtrate was precipitated for 30 minutes, the upper layer liquid was gently sucked off with a 20 ml syringe, and physiological saline was added for precipitation again, the supernatant was discarded, and the washing was repeated until there was no impurity. The worms were moved to EP tube and centrifuged at 1,000 rpm for 3 minutes to remove the excess liquid. 1 ml Trizol was added to the harvested worms and mixed well, and allowed to stand at room temperature for 5 minutes. 0.2 ml chloroform was added, the mixture was shaken vigorously for 15 s, incubated at room temperature for 2-3 min, and centrifuged at 12,000×g at 4° C. for 15 min. The upper layer was carefully collected, an equal volume of pre-cooled isopropanol was added, mixed, and incubated at room temperature for 10 min. The mixture was centrifuged at 12,000×g at 4° C. for 10 min, and the supernatant was discarded. 1 ml 75% ethanol (prepared with DEPC-treated water) was added to the pellet, gently shaken for 15 seconds, centrifuged at 7,500×g at 4° C. for 5 minutes, and the supernatant was carefully discard. The precipitate was placed at room temperature and dried for 3-5 minutes, 20-30 μl DEPC-treated water was added to dissolve the precipitate, and then stored at −20° C.

The extracted total RNA was used for reverse transcription to synthesize cDNA. The reaction system was as follows:

| | |
|---|---|
| M-MLV 5 × Reaction Buffer | 5.0 μl |
| dNTP Mixture | 1.0 μl |
| M-MLV RT | 1.0 μl |
| RNAase inhibitor | 0.5 μl |
| oligo dT$_{18}$ | 1.0 μl |
| RNAase-free H$_2$O | Up to 25 μl |

The reaction system was mixed well in reacted at 42° C. for 1 hour, and then stored at −20° C.

3. Construction of pET28a-Ts-WN10 Expression Vector

The Ts-WN10 gene was amplified using the cDNA obtained by reverse transcription as a template. The PCR reaction system (50μl) was as follows:

| | |
|---|---|
| 10 × Ex Taq Buffer | 5.0 μl |
| 10 mM dNTPs | 1 μl |
| Ex Taq | 0.5 μl |
| 10 pM Forward Primer | 2 μl |
| 10 pM Reverse Primer | 2 μl |
| cDNA Template | 3 μl |
| Sterile ddH$_2$O | 36.5 μl |

The reaction conditions: 95° C. pre-denaturation for 5 minutes; 95° C. for 45 s, 53° C. for 45 s, 72° C. for 45 s, 30 cycles; 72° C. final extension for 10 minutes. The amplified product showed a band around 1161 bp in the 1% agarose gel electrophoresis (FIG. 1), which is consistent with the expected size of the target product. The PCR product was recovered by gel extraction. Sequencing result showed that the gene fragment encoding Ts-WN10 protein was successfully obtained.

The result of cloning experiment for Ts-WN10 gene (FIG. 1) showed that the Ts-WN10 gene fragment was amplified by specific primers, and the sequence was of 1161 bp without the signal peptide coding part.

The Ts-WN10 fragment recovered from the gel was subjected to double digestion, and the digestion system was as follows:

| | |
|---|---|
| 10 × H Buffer | 2 μl |
| EcoRI | 2 μl |
| XhoI | 2 μl |
| WN10 Fragment | 10 μl |
| Sterile ddH$_2$O | 4 μl |

The prokaryotic expression vector pET28a was subjected to double digestion, and the digestion system was as follows:

| | |
|---|---|
| 10 × H Buffer | 2 μl |
| EcoRI | 2 μl |
| XhoI | 2 μl |
| pET28a Vector | 10 μl |
| Sterile ddH$_2$O | 4 μl |

The digestion reaction system was put into a 37° C. water bath for 2 hours, and then subjected to gel purification. The digested WN10 fragment was ligated with pET28a vector, and the reaction system was:

| | |
|---|---|
| 10 × T$_4$DNA Ligase Buffer | 1 μl |
| Digested WN10 fragment | 4 μl |
| Digested pET28a | 1.5 μl |
| T$_4$DNA Ligase | 1 μl |
| ddH$_2$O | 2.5 μl |

The ligation was carried out at 16° C. overnight. All ligation products were transformed into E. coli DH5α competent cells, and single colonies were picked for double enzyme digestion identification. The positive recombinant plasmid was transformed into BL21 (DE3) competent cells.

4. Expression and Purification of Ts-WN10

1 ml of broth containing recombinant bacteria was added to 100 ml of LB medium and cultured at 37° C. with shaking until O.D. 600 nm value was about 0.5-1. IPTG was added to a final concentration of 1 mmol/L, and the culture was induced at 37° C. for 6-8 h. The expressed products were subjected to SDS-PAGE electrophoresis and purified by cutting the gel. An appropriate amount of PBS was added to the gel, and the gel was ground into crushed particles, which can be used to immunize mice.

5. Induced Expression of Ts-WN10 and One-Step On-Column Purification and Refolding The broth after induction was centrifuged and resuspended in 30 mL resuspension buffer (20 mM Tris-HCl PH 8.0). The mixture was placed in an ice bath for 10 minutes, and sonicated on ice (3 seconds sonication and 3 seconds interval for a total of 30 minutes). The mixture was centrifuged at 8,000 rpm for 10 min to collect the precipitate, and the precipitate was resuspended in 30 ml of pre-cooled inclusion body washing solution (2M urea, 20 mM Tris-HCl, 0.3M NaCl pH 8.0), put on ice for 10 min, and sonicated on ice (3 seconds sonication and 3 seconds interval for a total of 30 minutes). This step was repeated 3 times. The mixture was centrifuged at 8,000 rpm for 10 minutes to collect the precipitate, and the precipitate was resuspended in 30 ml of pre-cooled PBS washing solution (0.01M PBS containing 4M urea), put on ice for 10 min, and sonicated on ice (3 seconds sonication and 3 seconds interval for a total of 30 minutes). This step was repeated 2 times. The mixture was centrifuged at 8,000 rpm for 10 min to collect the precipitate, and the precipitate was resuspended in 5 ml binding buffer (8M urea, 20 mM Tris-HCl, 0.3M NaCl, 5 mM imidazole pH 8.0) and dissolved overnight at 4° C. The mixture was centrifuged at 8,000 rpm for 30 min to collect the supernatant, and the supernatant was filtered and used for sample loading. Refer to the "Purifying Challenging Proteins" pages 77-79 of manual (GE Healthcare) for the refolding procedure on the AKTA protein purification system. Purification column has 1 ml HisTrap' HP. After loading the sample, the refolding time on the column was 2 h, and the solution was 100% replaced with Refolding Buffer (20 mM Tris-HCl, 0.3M NaCl, 5 mM imidazole, 1 mM 2-mercaptoethanol pH 8.0) solution. The solution was changed to Elution Buffer (20 mM Tris-HCl, 0.3M NaCl, 500 mM imidazole pH 8.0) to elute the target protein. The above purification experiment was repeated on 4 batches of culture.

The UV absorption spectrum for the Ts-WN10 protein refolding on column showed that after the solution was 100% replaced with the Refolding Buffer, and washed the column with 5 column volumes of the Refolding Buffer, an obvious elution peak appeared. After the solution was exchanged to Elution Buffer, obvious elution peaks also appeared. SDS-PAGE results showed that both of the two peaks were the elution peak of the target protein. In the 4 repeat purification experiments, the SDS-PAGE results showed that a highly uniform soluble target protein was obtained in each experiment.

Figure 2:
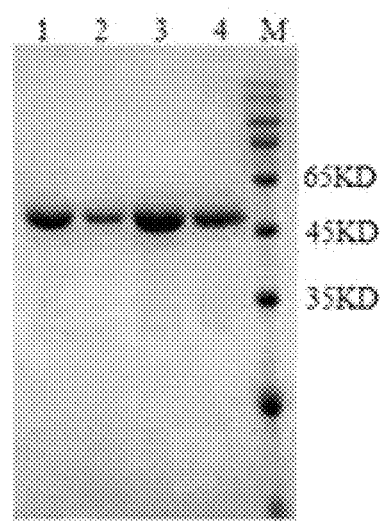
FIG. 2 shows the SDS-PAGE results of purified Ts-WN10 protein; M, protein molecular marker; 1-4, 1-4 batches of purified Ts-WN10 protein.

It can be seen from the results of SDS-PAGE that the supernatant of the purified protein showed only one clear band, and the size was consistent with the theoretical value (FIG. 2), indicating that the present invention has obtained relatively pure recombinant Ts-WN10 (rTs-WN10) soluble protein. Using the BCA protein quantification kit, the concentration of the above-mentioned purified protein was determined, and the concentration of rTs-WN10 protein was 1 to 0.65 mg/mL.

Example 2 Preparation of Anti-Ts-WN10 Monoclonal Antibody

1. Immunization of Mice

The purified rTs-WN10 protein was used to immunize five 6-week-old female BALB/c mice. The immunization was carried out 5 times. The immunization interval was two weeks. The immunization dose was 50μg/mouse. The immunization route was intraperitoneal immunization.

Blood samples were collected from the tail of the mice one week after the fourth and the fifth immunizations, and the serum was separated (4° C., 3,000 rpm centrifugation for 30 min). Antibody levels were detected by Ts-WN10 and indirect ELISA method. The indirect ELISA was performed as follows: the purified and refolding Ts-WN10 protein was diluted with a coating solution (0.01M NaOH, pH 12), and the coating amount was 0.125μg/well, 100 μl per well. Coating was carried out at 37° C. for 2 h or 4° C. overnight. The plate was washed 3 times with PBST (containing 0.05% Tween 20), and then blocked with a blocking buffer (5% non-fat milk) at 37° C. for 2 hours. The plate was washed 3 times with PBST. The serum to be tested (or hybridoma supernatant in other experiments) was diluted (at a 2-fold ratio) and added to the plate with 100 μl per well. After incubating at 37° C. for 1 hour, the plate was washed 3 times with PB ST. The goat anti-mouse secondary antibody was diluted 1:1000 and incubated with the plate at 37° C. for 30 min. The plate was washed 4 times with PBST. The plate was developed at 37° C. for 10 minutes, and the reaction was terminated with 2M $H_2SO_4$. The absorbance value at O.D. 450 nm was recorded.

Three days before the cell fusion, BALB/c mice with high anti-Ts-WN10 level were boosted, and each mouse was injected with 50 μg immunogen into the abdominal cavity.

2. Cell Fusion

Feeder cells were prepared one day before fusion. Macrophages from BALB/c mouse were collected according to conventional methods and plated in 96-well cell culture plates for later use. The mice were sacrificed by cervical dislocation, the spleen was taken out under aseptic conditions, and the spleen cells were isolated. $1 \times 10^8$ spleen cells were mixed with $2.5 \times 10^7$ SP2/0 myeloma cells at a ratio of 4:1. 1 ml PEG1000 was added to the plate for cell fusion, and the dripping was over within 1 min. Then, within 1 min, 1 ml of 1640 basal medium preheated to 37° C. was added dropwise to the cell suspension with stirring. Furthermore, within 3 minutes, 1 ml of 1640 basal medium preheated to 37° C. was added dropwise to the cell suspension with stirring. Finally, 10 ml of 1640 basal medium at 37° C. was slowly added to the cell suspension. The whole process was operated in a 37° C. water bath. The cell suspension was centrifuged at 1,000 rpm for 10 min, the supernatant was discarded, and the cells were resuspended in HAT medium. The cells were evenly spread into a 96-well plate pre-plated with feeder cells, and placed in a 37° C., 5% CO2 incubator for culture.

3. Screening and Cloning of Positive Hybridoma Cell Lines

The Ts-WN10 and indirect ELISA were used to screen positive hybridoma cells, and the positive hybridoma cells were expanded and cultured. The first subcloning of the positive hybridoma cells was performed by the limiting dilution method. Refer to the ES indirect ELISA method described in Chapter 2.1.20-Trichinellosis of OIE Terrestrial Manual 2017, to screen the positive hybridoma cell lines again, to expand the culture of the positive hybridoma cells, and to subclone the positive hybridoma cells by the limiting dilution method. The subcloning was performed at least 3 times, and the subcloned positive hybridoma cell lines were frozen. Finally, a hybridoma cell line that can stably generate anti-Ts-WN10 monoclonal antibody was obtained, which was named WN10-1H9, with a deposit number of CGMCC No. 18316. The antibody generated by WN10-1H9 cell line was named WN10-1H9-Ab (1H9 for short).

WN10-1H9 was subjected to sequencing followed the standard protocol in the art. The amino acid sequence of the light chain variable region of the antibody is

```
                                          (SEQ ID NO: 15)
DVVVTQSPASLAVSLGQRATISCRASKSVDNYGISFMNWFQQKPGQPPKL

LIYAASNQGSGVPARFSGSGSGTDFSLNIHPMEEDDTAMYFCQQIKEVPY

TFGGGTKLEIK;
``` and the amino acid sequence of the heavy chain variable region of the antibody is

```
                                          (SEQ ID NO: 16)
QVQLQQPGSELVRPGASVKLSCKASGYTFTSYWMHWVKQRPGQGLEWIGN

ISPGSGNTNYDEKFKTKATLTVDTSSSTAYMQLSSLTSEDSAVYYCTRHG

TVDYWGQGTTVTVSS.
```

Complementarity-determining regions (CDRs) are shown below:

```
CDR-L1:
                 (SEQ ID NO: 17)
KSVDNYGISF;

CDR-L2:
                 (SEQ ID NO: 18)
AAS;

CDR-L3:
                 (SEQ ID NO: 19)
QQIKEVPYT;

CDR-H1:
                 (SEQ ID NO: 20)
GYTFTSYW;

CDR-H2:
                 (SEQ ID NO: 21)
ISPGSGNT;

CDR-H3:
                 (SEQ ID NO: 22)
TRHGTVDY.
```

4. Preparation of Ascites Containing Antibodies

Healthy BALB/c mice about 12 weeks of age were intraperitoneally injected with paraffin oil, 0.5 ml/mouse. One week later, the mice were intraperitoneally injected with $1\times10^6$ hybridoma cells. After 7 to 10 days, when the mouse's belly was extremely big, the ascites was collected every 2 days. The extracted ascites was centrifuged at 10,000 rpm for 10 min to remove the upper layer of grease and sediment, and the supernatant was aliquoted and stored at −20° C.

Example 3 Identification of Monoclonal Antibody

1. Subclass Identification of Monoclonal Antibody

The monoclonal antibodies obtained in Example 2 was subjected to subclass identification according to the instructions of the antibody subclass identification kit. The results show that the heavy chains of the monoclonal antibodies of the present disclosure are all IgG1, and the light chains are kappa chains. See Table 1 for details.

TABLE 1

| Subclass identification of monoclonal antibody | | | | | | | | |
|---|---|---|---|---|---|---|---|---|
| Subclass | IgG1 | IgG2a | IgG2b | IgG3 | IgM | IgA | κ chain | λ chain |
| OD 450 nm | 0.837 | 0.062 | 0.045 | 0.048 | 0.031 | 0.046 | 0.757 | 0.039 |

2. Competitive ELISA

Coating and blocking were performed the same as indirect ELISA. Sera of pig infected with or without *Trichinella spiralis* were diluted at a 2-fold ratio starting from 1:1. After dilution, 50µl of each serum was mixed with 50µl of monoclonal antibody supernatant in equal volume. After mixing, 100 µl of the solution was added to the plate and incubated at 37° C. for 1 h. The following steps were the same as indirect ELISA. The analysis was performed to see whether the monoclonal antibody could compete with the positive serum of pig infected with *Trichinella spiralis* to bind to the Ts-WN10 protein.

Figure 3:
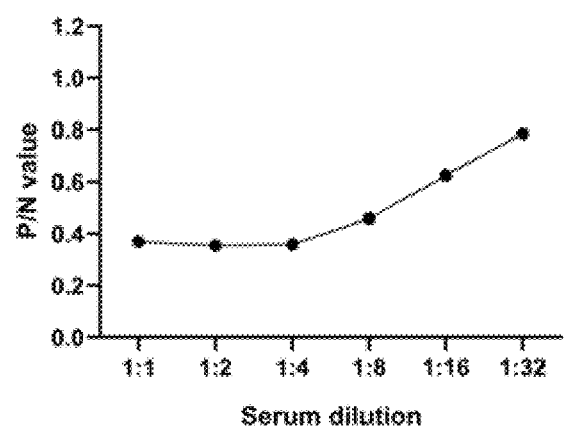
FIG. 3 shows that Ts-WN10 antigen competition assay of 1H9 monoclonal antibody and the positive serum of pig infected with *Trichinella spiralis*.

The test results show that the monoclonal antibody prepared by the present disclosure can compete with the positive serum of pig infected with *Trichinella spiralis* to bind to the Ts-WN10 protein, as shown in Table 2 and FIG. 3. As shown in FIG. 3 that the P/N value of the monoclonal antibody increases with the increase of the dilution of the *Trichinella spiralis* positive serum, indicating that the *Trichinella spiralis* positive serum can block the monoclonal antibody. Therefore, the monoclonal antibody is a competing antibody of the antibodies in pig serum.

TABLE 2

1H9 monoclonal antibody competes with *Trichinella spiralis*-infected pig serum for binding to Ts-WN10 antigen

| | Dilutions of Sera | | | | | |
|---|---|---|---|---|---|---|
| | 1:1 | 1:2 | 1:4 | 1:8 | 1:16 | 1:32 |
| OD 450 nm of positive serum (P) | 0.3470 | 0.3065 | 0.2700 | 0.3480 | 0.5680 | 0.7685 |
| OD 450 nm of negative serum (N) | 0.9380 | 0.8650 | 0.7525 | 0.7590 | 0.9080 | 0.9775 |
| P/N Value | 0.369936 | 0.354335 | 0.358804 | 0.458498 | 0.625551 | 0.786189 |

3. Western Blot Experiments

*Trichinella spiralis* muscle larvae were washed 3 times with ddH$_2$O, and a small amount of ddH$_2$O was added. In an ice bath, the worms were grinded to pieces by a tissue grinder, and then broken by an ultrasonic cell pulverizer on ice (voltage: 300V; ultrasonication: 5 s; interval: 9 s; operation: 5 times; total 3 cycles). Observing under the light microscope, when the worm bodies were crushed into smaller pieces, it was placed at 4° C. and −20° C. alternately for freeze-thaw lysis, 5 times. After freeze-thaw lysis, the mixture was centrifuged at 4° C. at 1,600 g for 30 minutes, and the supernatant was collected as the soluble antigen. The supernatant was subjected to SDS-PAGE electrophoresis, and then transferred to a nitrocellulose membrane. The membrane was blocked with 5% non-fat milk at 4° C. overnight. Monoclonal antibody was added and incubated at room temperature for 1 hour. The membrane was washed 3 times with PBST, and then incubated with HRP-labeled goat anti-mouse IgG antibody (diluted at 1:3000) for 1 h at room temperature. After the membrane was washed 3 times with PBST, ECL luminescent substrate was added for color development. The cell culture medium was used as a negative control.

Figure 4:
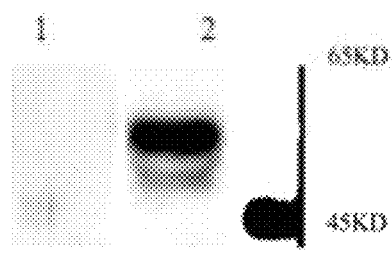
FIG. 4 shows the Western blot analysis of the anti-Ts-WN10 monoclonal antibody to the soluble antigen of the *Trichinella spiralis*; M, protein molecular marker; 1, cell culture medium; 2, 1H9 monoclonal antibody.

The test results show that the monoclonal antibody can bind to the soluble antigen from the worms, and the position of the recognized band is consistent with the position of WN10, indicating that the obtained monoclonal antibody can recognize the natural WN10 antigen. The monoclonal antibody 1H9 prepared by the present disclosure can specifically react with the soluble antigen of *Trichinella spiralis* muscle larvae (FIG. 4).

Example 4 Identification of B-Cell Epitope

1. Expression of Truncated Ts-WN10 Protein (1$^{st}$ Round)

Using the sequence of the recombinant plasmid pET28a-WN10 as a template, 2 pairs of primers were designed:

```
TsWN10-A-EcoRI-atg:
5'-TAACGAATTCATGCAGATACTTGGTGA-3'
(as shown in SEQ ID No: 5);

TsWN10-A-XhoI-tta:
5'-GACGCTCGAGTTAATTCACCCTT-3'
(as shown in SEQ ID No: 6);

TsWN10-B-EcoRI-atg:
5'-TAACGAATTCATGCGTGTCCAAAGG-3'
(as shown in SEQ ID No: 7);

TsWN10-B-XhoI-tta:
5'-GACGCTCGAGTTAACATTCAACA-3'
(as shown in SEQ ID No: 8).
```

Figure 5:
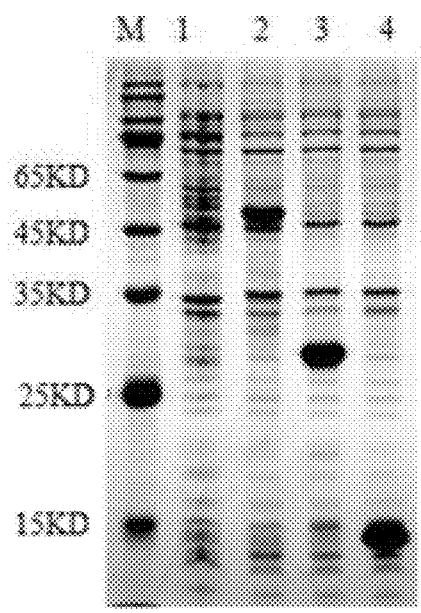
FIG. 5 shows the SDS-PAGE analysis of Ts-WN10-A and Ts-WN10-B protein expression. M, protein molecular marker; 1, BL21-pET28a (after IPTG induction); 2, BL21-pET28a-WN10 (after IPTG induction); 3, BL21-pET28a-WN10-A (after IPTG induction); 4, BL21-pET28a-WN10-B (after IPTG induction).
Figure 6:
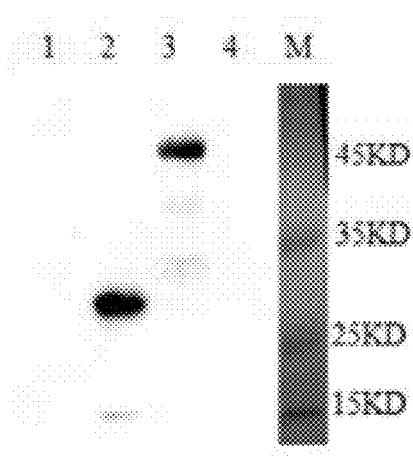
FIG. 6 shows the Western blot analysis of WN10-A and WN10-B. M, protein molecular marker; 1, Western blot result of WN10-B and 1H9; 2, Western blot result of WN10-A and 1H9; 3, Western blot result of WN10 and 1H9.

WN10 fragments A and B were obtained by PCR amplification respectively and ligated into pET28a vector to construct recombinant plasmids, named pET28a-WN10-A and pET28a-WN10-B, respectively. Recombinant bacteria containing pET28a-WN10-A or pET28a-WN10-B was induced separately to express the recombinant proteins, according to step 4 in Example 1. The expression products were analyzed by SDS-PAGE electrophoresis to confirm that the proteins were successfully expressed. These two proteins were subjected to SDS-PAGE, and the Western blot was performed using the monoclonal antibody according to the method of Example 3. The results showed that the B-cell epitope targeted by the monoclonal antibody 1H9 was located in the WN10-A fragment (FIG. 5 and FIG. 6).

2. Expression of Truncated Ts-WN10 Protein (2$^{nd}$ Round)

Using the sequence of the recombinant plasmid pET28a-WN10-A as a template, two pairs of primers were designed, and the PCR amplification products were inserted into the pET28a vector according to the method in Example 1 to construct recombinant plasmids, respectively named pET28a-WN10-A01 and pET28a-WN10-A02. Recombinant proteins were expressed according to the method of Example 1. The expression products were analyzed by SDS-PAGE electrophoresis to confirm that the proteins were successfully expressed. These two proteins were subjected to SDS-PAGE, and the Western blot was performed using the monoclonal antibody according to the method of Example 3. The results showed that the B-cell epitope targeted by the monoclonal antibody 1H9 was located in the WN10-A01 fragment (FIG. 7 and FIG. 8).

Primers are shown below.

```
TsWN10-A01-EcoRI-atg:
5'-TAACGAATTCATGCAGATACTTG-3'
(as shown in SEQ ID No: 9);

TsWN10-A01-XhoI-tta:
5'-GACGCTCGAGTTAAGCATTTGAA-3'
(as shown in SEQ ID No: 10);

TsWN10-A02-EcoRI-atg:
5'-TAACGAATTCATGATTGATTCAAATGC-3'
(as shown in SEQ ID No: 11);

TsWN10-A02-XhoI-tta:
5'-GACGCTCGAGTTAATTCACCCTT-3'
(as shown in SEQ ID No: 12).
```

SDS-PAGE analysis showed that both proteins were successfully expressed. It was identified by Western blot that 1H9 monoclonal antibody reacted specifically with Ts-WN10-A01, and the reactivity was strong.

3. Identification of Epitope Recognized by the Monoclonal Antibody

The software DNAstar was used to predict the hydrophilicity and antigenicity of WN10, and the epitope prediction programs ABpred and Bepipred were used to predict the epitopes. 14 short peptides were synthesized using PepScan technology. These short peptides were tested by indirect ELISA, and the coating amount was 0.25 μg/well. The results showed that 1H9 reacted specifically with Ts-WN10-W2. Based on the results of Western blot, it is inferred that the B-cell epitope of Ts-WN10 recognized by 1H9 is the amino acid sequence VNCQGEGRRKHCTME (SEQ ID NO: 1).

TABLE 3

| Synthetic Peptides | | |
|---|---|---|
| Peptide | Sequence | SEQ ID NO: |
| W1 | ALFSSDLKQESGVFH | 23 |
| W2 | VNCQGEGRRKHCTME | 24 |
| W3 | TMEYTHRNPSKATVS | 25 |

TABLE 3-continued

| Synthetic Peptides | | |
|---|---|---|
| Peptide | Sequence | SEQ ID NO: |
| W4 | TVSKCFEEVEEPLII | 26 |
| W5 | QILGETTHYGRNDP | 27 |
| W6 | ALFSSDSKEQSGVLH | 28 |
| W7 | HKLVELEESSTMGIL | 29 |
| W8 | CTLEYRHRTPSTATV | 30 |
| W9 | EEQVVSQRSQMLGGT | 31 |
| W10 | IFESDKKKSSGTYLL | 32 |
| W11 | KETECGIKEKAFNSY | 33 |
| W12 | EKAFNSYEDVYKNCS | 34 |
| W13 | DVYKNCSGSGDSKVC | 35 |
| W14 | VEYKYFDPTKSTVEC | 36 |

TABLE 4

| Indirect ELISA results of peptides with WN10-1H9-Ab | | | | | | | |
|---|---|---|---|---|---|---|---|
| | Peptide No. | | | | | | |
| | W1 | W2 | W3 | W4 | W5 | W6 | W7 |
| OD 450 nm | 0.0733 | 1.1533 | 0.1487 | 0.1714 | 0.2860 | 0.1273 | 0.1616 |
| | Peptide No. | | | | | | |
| | W8 | W9 | W10 | W11 | W12 | W13 | W14 |
| OD 450 nm | 0.1516 | 0.1441 | 0.1610 | 0.1470 | 0.1600 | 0.1663 | 0.1581 |

The above are only the preferred embodiments of the present disclosure. It should be noted that for those of ordinary skill in the art, without departing from the principle of the present invention, several improvements and modifications can be made, and these improvements and modifications are also It should be regarded as the protection scope of the present invention.

What is claimed is:

1. An antibody or antigen-binding fragment thereof capable of specifically binding to *Trichinella spiralis* WN10 protein, comprising
   a CDR-L1, a CDR-L2, and a CDR-L3 in a light chain variable region, and
   a CHR-H1, a CDR-H2, and a CDR-H3 in a heavy chain variable region,
   wherein the CDR-L1, CDR-L2 and CDR-L3 have an amino acid sequence set forth in SEQ ID NOs: 17, 18 and 19, respectively, and
   wherein the CDR-H1, CDR-H2 and CDR-H3 have an amino acid sequence set forth in SEQ ID NOs: 20, 21 and 22, respectively.

2. The antibody or antigen-binding fragment thereof according to claim 1 comprising a light chain variable region with a sequence set forth in SEQ ID NO: 15 and a heavy chain variable region with a sequence set forth in SEQ ID NO: 16.

3. The antibody or antigen-binding fragment thereof according to claim 1, wherein the antibody comprises a constant region sequence of mouse IgG1.

4. The antibody or antigen-binding fragment thereof according to claim 1, wherein the antigen-binding fragment comprises one or more selected from the group consisting of F(ab')$_2$, Fab', Fab, Fv and scFv.

5. A kit for detecting *Trichinella spiralis* comprising the antibody or antigen-binding fragment thereof according to claim 1 and an instruction for use.

6. A hybridoma cell line deposited at China General Microbiological Culture Collection Center (CGMCC) with an accession number of 18316.

* * * * *